US012710347B2

(12) United States Patent
Makise et al.

(10) Patent No.: US 12,710,347 B2
(45) Date of Patent: Aug. 18, 2026

(54) METHOD OF MEASURING CONTACT ANGLE OF SILICON WAFER AND METHOD OF EVALUATING SURFACE CONDITION OF SILICON WAFER

(71) Applicant: SUMCO Corporation, Tokyo (JP)

(72) Inventors: Sayaka Makise, Tokyo (JP); Ryosuke Takahashi, Tokyo (JP); Mami Kubota, Tokyo (JP); Noritomo Mitsugi, Tokyo (JP); Shuichi Samata, Tokyo (JP)

(73) Assignee: SUMCO CORPORATION, Tokyo (JP)

(*) Notice: Subject to any disclaimer, the term of this patent is extended or adjusted under 35 U.S.C. 154(b) by 303 days.

(21) Appl. No.: 18/579,603

(22) PCT Filed: Jun. 29, 2022

(86) PCT No.: PCT/JP2022/026091
§ 371 (c)(1),
(2) Date: Jan. 16, 2024

(87) PCT Pub. No.: WO2023/017692
PCT Pub. Date: Feb. 16, 2023

(65) Prior Publication Data

US 2024/0344951 A1 Oct. 17, 2024

(30) Foreign Application Priority Data

Aug. 12, 2021 (JP) ................................ 2021-131787

(51) Int. Cl.
*G01N 13/02* (2006.01)
*G01N 33/00* (2006.01)

(52) U.S. Cl.
CPC ......... *G01N 13/02* (2013.01); *G01N 33/0095* (2024.05); *G01N 2013/0208* (2013.01); *G01N 2013/0241* (2013.01)

(58) Field of Classification Search
CPC ............... G01N 13/02; G01N 33/0095; G01N 2013/0208; G01N 2013/0241; H10P 52/00; H10P 74/203; H10P 74/20
See application file for complete search history.

(56) References Cited

U.S. PATENT DOCUMENTS

2003/0102017 A1 6/2003 Taniyama
2008/0177022 A1 7/2008 Yamasaki et al.
(Continued)

FOREIGN PATENT DOCUMENTS

JP H06-216098 A 8/1994
JP 3049453 U 6/1998
(Continued)

OTHER PUBLICATIONS

Tommi Huhtamaki, Surface wetting characterization using contact angle measurements, 2018, Nature Protocols, vol. 13, pp. 1521-1538 (Year: 2018).*

(Continued)

*Primary Examiner* — Francis C Gray
(74) *Attorney, Agent, or Firm* — GREENBLUM & BERNSTEIN, P.L.C.

(57) ABSTRACT

A method of measuring the contact angle of a silicon wafer according to the present disclosure can detect differences in the severe hydrophilicity level of the silicon wafer surface, such differences not being detectable by contact angle measurement using pure water. The method of measuring a contact angle of a silicon wafer includes dripping a droplet on a surface of a silicon wafer, and measuring a contact angle of the surface of the silicon wafer from an image of the droplet. The droplet includes an aqueous solution having a surface tension greater than a surface tension of pure water.

10 Claims, 2 Drawing Sheets

(56) References Cited

U.S. PATENT DOCUMENTS

| | | | | |
|---|---|---|---|---|
| 2009/0258211 | A1 | 10/2009 | Yoshinaga et al. | |
| 2019/0285530 | A1* | 9/2019 | Behroozi | G01N 13/02 |
| 2020/0061772 | A1* | 2/2020 | Tanaka | B24B 37/08 |
| 2024/0290665 | A1* | 8/2024 | Takahashi | H10P 52/00 |

FOREIGN PATENT DOCUMENTS

| | | | | | |
|---|---|---|---|---|---|
| JP | 2003-168668 | A | | 6/2003 | |
| JP | 2005-127988 | A | | 5/2005 | |
| JP | 2008088258 | A | * | 4/2008 | |
| JP | 2009-074142 | A | | 4/2009 | |
| WO | 2008/013151 | A1 | | 1/2008 | |
| WO | WO-2014000739 | A1 | * | 1/2014 | G01N 13/02 |
| WO | WO-2021036716 | A1 | * | 3/2021 | B01D 69/02 |

OTHER PUBLICATIONS

Behrooz Khatir, Design and High-Resolution Characterization of Silicon Wafer-Like Omniphobic Liquid Layers Applicable to any Substrate, 2020, TSpace Reseach Repository, tspace.library.utoronto.ca (Year: 2020).*

ISR issued in International Patent Application No. PCT/JP2022/026091, Sep. 20, 2022, translation.

IPRP issued in International Patent Application No. PCT/JP2022/026091, Feb. 13, 2024, translation.

Office Action issued in TW Patent Application No. 111126986, Mar. 8, 2023, translation.

Zhong et al., “Wettability Effect on Evaporation Dynamics and Crystalline Patterns of Sessile Saline Droplets, vol. 121”, Droplets, J. Physical Chemistry B, ACS Publications, Jul. 20, 2017, pp. 7924-7933.

Office Action issued in JP Patent Application No. 2021-131787, Sep. 17, 2024, translation.

Office Action issued in KR Patent Application No. 10-2023-7042757, Aug. 13, 2025, translation.

Office Action issued in Chinese Patent Application No. 202280054856.X, Mar. 14, 2025, translation.

* cited by examiner

FIG. 1

Liquid

Solid

Gas

Endpoint $\gamma_L$ $\gamma_{SL}$ $\gamma_S$ $\theta$ $\gamma_L \cos\theta$ $\gamma_S = \gamma_L \cos\theta + \gamma_{SL}$

METHOD OF MEASURING CONTACT ANGLE OF SILICON WAFER AND METHOD OF EVALUATING SURFACE CONDITION OF SILICON WAFER

TECHNICAL FIELD

The present disclosure relates to a method of measuring the contact angle of a silicon wafer and a method of evaluating the surface condition of a silicon wafer.

BACKGROUND

One known method for evaluating the surface condition of a silicon wafer is to drip a drop of pure water on the surface of the silicon wafer and measure the contact angle of the silicon wafer surface from an image of the dripped drop.

For example, in Patent Literature (PTL) 1 (see Example 7), a wafer was washed at 70° C. for 10 minutes using SC-1, to which the chelating agent TTHA was added, and was then rinsed with pure water heated to 50° C., to which 100 ppm of HF was added. The change in water droplet contact angle versus rinse time was examined. Here, when the rinse time was 30 minutes or less, the water droplet contact angle was 5°, which was thought to indicate that a natural oxide film remained on the wafer surface. Conversely, when the rinse time was 120 minutes, the water droplet contact angle was 60°, which was thought to indicate that the natural oxide film on the wafer surface had been removed, exposing the bare silicon surface. The contact angle of a wafer surface has thus been measured with a water droplet to determine whether the wafer surface is hydrophilic or hydrophobic.

CITATION LIST

Patent Literature

PTL 1: JP H6-216098 A

SUMMARY

Technical Problem

As is clear from PTL 1, in a case in which a natural oxide film is formed on the wafer surface, the wafer surface is basically hydrophilic, and the contact angle of the wafer surface is generally 5° or less when measured with a drop of pure water. However, we focused on the novel issue of detecting differences in the severe hydrophilicity level of wafer surfaces that do not exhibit a difference in the contact angle value of the wafer surface as measured with pure water. No known technology for resolving this issue could be found.

It could be helpful to provide a method of measuring the contact angle of a silicon wafer that can detect differences in the severe hydrophilicity level of the silicon wafer surface, such differences not being detectable by contact angle measurement using pure water.

Solution to Problem

To solve the aforementioned problem, we conceived of measuring the contact angle of a silicon wafer surface using a droplet composed of an aqueous solution having a surface tension larger than the surface tension of pure water. The reason for this approach is that if the contact angle of the wafer surface is measured with an aqueous solution having a larger surface tension than the surface tension of pure water, a larger measurement value of the contact angle can be obtained than when measuring the contact angle with pure water. We thus thought this would enable detection of differences in the severe hydrophilicity level of the wafer surface, such differences not being detectable by contact angle measurement using pure water. As a result of experiments, we confirmed that differences in the severe hydrophilicity level can be detected by measuring the contact angle of a silicon wafer surface using a droplet composed of an aqueous solution having a surface tension greater than the surface tension of pure water.

We provide the following.

[1] A method of measuring a contact angle of a silicon wafer, the method including:

dripping a droplet on a surface of a silicon wafer; and measuring a contact angle of the surface of the silicon wafer from an image of the droplet, wherein the droplet is composed of an aqueous solution having a surface tension greater than a surface tension of pure water.

[2] The method of measuring a contact angle of a silicon wafer according to [1], wherein the aqueous solution is at least one selected from the group consisting of a sodium chloride solution, a potassium chloride solution, and a magnesium chloride solution.

[3] The method of measuring a contact angle of a silicon wafer according to [1] or [2], wherein the aqueous solution has a concentration of 10 mass % or more.

[4] The method of measuring a contact angle of a silicon wafer according to any one of [1] to [3], wherein a volume of the droplet is in a range of 0.3 μL to 3.0 μL.

[5] The method of measuring a contact angle of a silicon wafer according to any one of [1] to [4], wherein the contact angle is measured in an environment with a humidity in a range of 30% RH to 70% RH.

[6] The method of measuring a contact angle of a silicon wafer according to any one of [1] to [5], further including measuring the contact angle of the surface of the silicon wafer under a plurality of conditions in which a volume of a droplet dripped on the surface differs and determining a relationship between the volumes of the droplet and measured values of the contact angle under the plurality of conditions.

[7] The method of measuring a contact angle of a silicon wafer according to [6], wherein the volume of the droplet is measured from the image of the droplet.

[8] The method of measuring a contact angle of a silicon wafer according to any one of [1] to [7], wherein the silicon wafer includes a surface layer that is an oxide film, and the oxide film forms the surface.

[9] The method of measuring a contact angle of a silicon wafer according to [8], wherein the oxide film is a natural oxide film.

[10] A method of evaluating a surface condition of a silicon wafer, the method including:

the method of measuring a contact angle of a silicon wafer according to any one of [1] to [9]; and evaluating a surface condition of the silicon wafer based on a value of the measured contact angle.

Advantageous Effect

The method of measuring the contact angle of a silicon wafer in the present disclosure enables detection of differences in the severe hydrophilicity level of the silicon wafer surface, such differences not being detectable by contact angle measurement using pure water.

BRIEF DESCRIPTION OF THE DRAWINGS

In the accompanying drawings:

FIG. 1 is a diagram illustrating Young's equation for a contact angle; and

Figure 2:
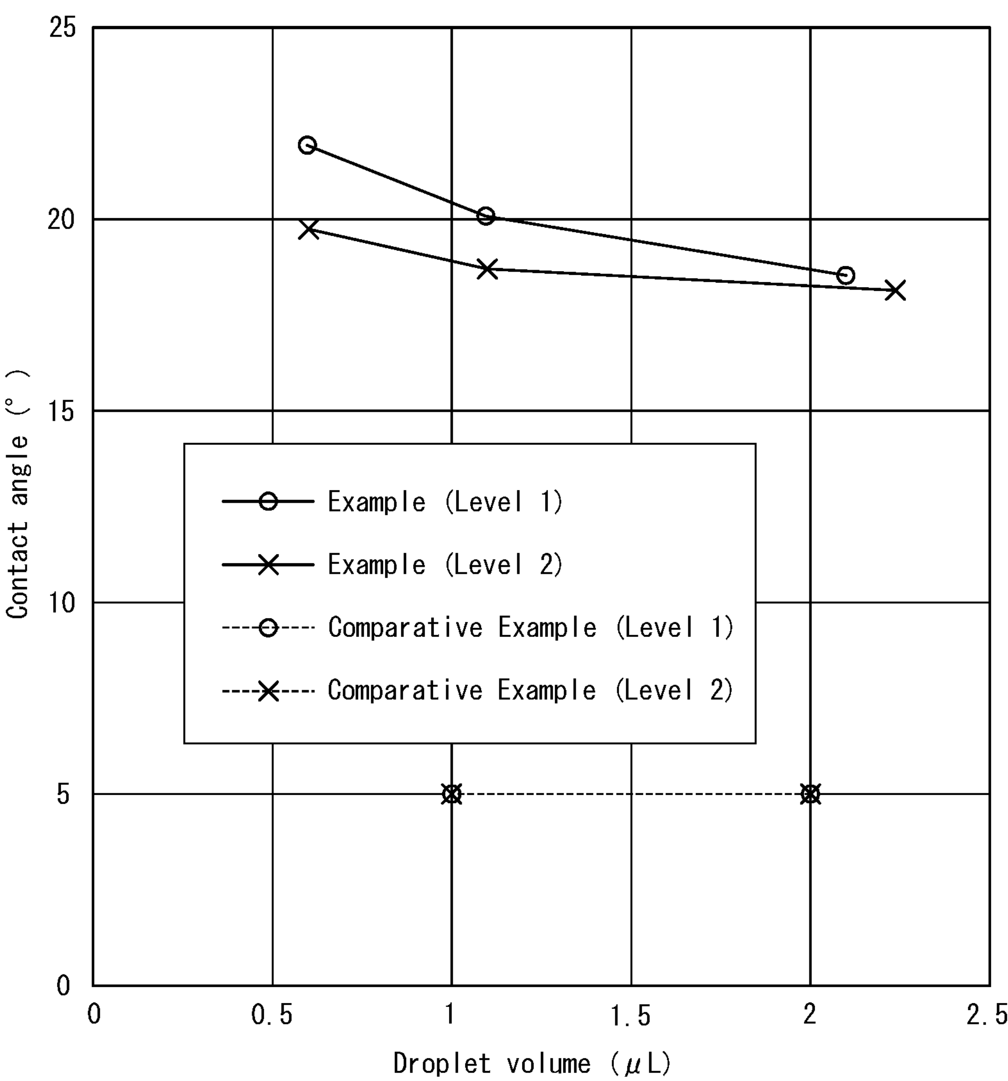
FIG. 2 is a graph illustrating the results of measuring the contact angle for Examples and Comparative Examples.

DETAILED DESCRIPTION (Method of Measuring Contact Angle of Silicon Wafer)

A method of measuring a contact angle of a silicon wafer according to an embodiment of the present disclosure includes dripping a droplet on a surface of a silicon wafer, and measuring a contact angle of the surface of the silicon wafer from an image of the droplet. The droplet is composed of an aqueous solution having a surface tension greater than a surface tension of pure water. According to the present embodiment, differences in the severe hydrophilicity level of the wafer surface can be detected, such differences not being detectable by contact angle measurement using pure water.

The silicon wafer used for the contact angle measurement in the present embodiment is suitably a single crystal silicon wafer. The surface layer of the silicon wafer is preferably an oxide film, and the oxide film preferably forms the surface of the silicon wafer. The oxide film is not particularly limited as long as the oxide film is a $SiO_2$ film. Examples include a thermal oxide film and a naturally oxidized film, but a naturally oxidized film is particularly preferable.

A suitable timing to apply the contact angle measurement method according to the present embodiment in the silicon wafer manufacturing process is immediately before single-wafer spin cleaning. Generally, the step immediately preceding single-wafer spin cleaning is a pre-cleaning step or an inspection step that follows the pre-cleaning step, and at the end of the pre-cleaning step, a natural oxide film is formed on the wafer surface. Specifically, in the pre-cleaning step, wafers are cleaned using a combination of an SC1 cleaning tank, an HF tank, an ozone tank, and the like and are then rinsed with pure water and subsequently dried. In the case of performing an inspection step, the wafer surface is inspected for particles, scratches, and the like, the wafer shape (flatness) is inspected, and so forth. In this way, the surface of the semiconductor wafer immediately before being subjected to single-wafer spin cleaning has a natural oxide film formed thereon, and the wafer surface is basically hydrophilic. Specifically, the contact angle of the wafer surface is generally 5° or less when measured by dripping pure water.

In practice, however, the level of hydrophilicity of the wafer surface varies, while not exhibiting a difference in the contact angle value of the wafer surface measured with pure water, depending on the storage conditions of the wafer before it is subjected to single-wafer spin cleaning. For example, after the aforementioned pre-cleaning step and optional inspection step, wafers are stored in a container called a Front-Opening Unified Pod (FOUP), and as the storage period becomes longer, minor deposition of organic matter may occur on the wafer surface. In addition, if drying after the aforementioned pre-cleaning step is insufficient, water vapor may be generated in the FOUP and adsorbed on the wafer surface, resulting in polarization of water molecules on the wafer surface. In the initial step of single-wafer spin cleaning (for example, spin cleaning with ozone water) of a wafer with such a degraded severe hydrophilicity level, the cleaning solution does not spread evenly over the wafer surface, and the film of cleaning solution is not continuously maintained on the wafer surface, yielding local areas of the wafer surface that the cleaning solution does not reach. As a result, particles remain after single-wafer spin cleaning or etching irregularities occur after single-wafer spin cleaning, resulting in a higher LPD count.

Therefore, the method of measuring the contact angle according to the present embodiment can be performed immediately before single-wafer spin cleaning, i.e., immediately after the aforementioned pre-cleaning step or the inspection step that follows the aforementioned pre-cleaning step. For silicon wafers that are determined, by the method of measuring the contact angle in the present embodiment, to have a degraded severe hydrophilicity level, measures such as pretreatment to increase the hydrophilicity of the wafer surface can be taken prior to single-wafer spin cleaning. In other words, the method of measuring the contact angle in the present embodiment can be considered an effective method for reliably reducing the LPD count after single-wafer spin cleaning.

Figure 1:
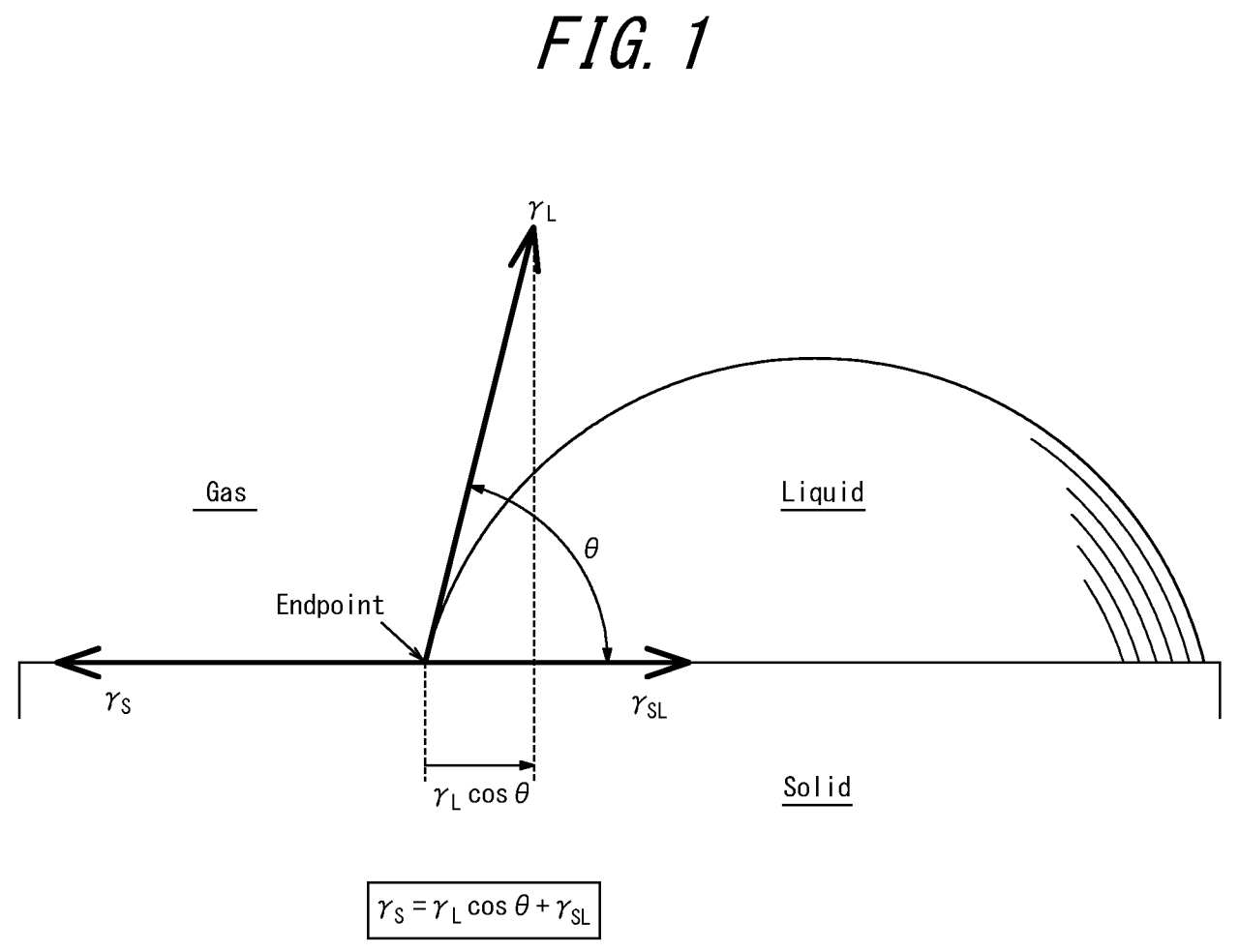

With reference to FIG. 1, the following Young's equation holds when a liquid is dripped onto a solid surface.

$$\gamma_S = \gamma_L \cdot \cos\theta + \gamma_{SL}$$

Here, $\gamma_S$ is the surface tension of the solid, $\gamma_{SL}$ is the interfacial tension between solid/liquid, $\gamma_L$ is the surface tension of the liquid, and $\theta$ is the contact angle.

$\gamma_S$ is the force pulling the endpoint in FIG. 1 to the left in an attempt to reduce the surface of the solid, i.e., the area of the gas/solid interface. $\gamma_{SL}$ is the force pulling the endpoint to the right in an attempt to reduce the area of the solid/liquid interface. $\gamma_L$ acts tangentially to the liquid contour in an attempt to reduce the surface of the liquid, i.e., the area of the gas/liquid interface, and the horizontal component thereof $\gamma_L \cdot \cos\theta$ pulls the endpoint to the right. When the droplet is at rest, these three forces are balanced, and Young's equation holds.

In the present embodiment, the contact angle needs to be measured by dripping a droplet composed of an aqueous solution having a surface tension $\gamma_{L2}$ greater than the surface tension $\gamma_{L1}$ of pure water onto the wafer surface. If the contact angle of the wafer surface is measured with an aqueous solution having a surface tension $\gamma_{L2}$ greater than the surface tension $\gamma_{L1}$ of pure water, a contact angle $\theta_2$ greater than the contact angle $\theta_1$ measured with pure water is obtained. This enables detection of differences in the severe hydrophilicity level of the wafer surface, such differences not being detectable by contact angle measurement using pure water. Specifically, an image of the droplet dripped on the surface of the semiconductor wafer is acquired, and the contact angle is measured from this image. The contact angle can be measured by a standard method. For example, the $\theta/2$ method, tangential method, or curve fitting method can be used.

The aqueous solution used in the present embodiment is preferably such that the interfacial tension $\gamma_{SL2}$ between the silicon wafer surface ($SiO_2$) and the aqueous solution is equal to or greater than the interfacial tension $\gamma_{SL1}$ between the silicon wafer surface ($SiO_2$) and pure water. This ensures that a contact angle $\theta_2$ greater than the contact angle $\theta_1$ measured with pure water can be reliably obtained. It is difficult to actually measure $\gamma_{SL1}$ and $\gamma_{SL2}$. However, the surface tension $\gamma_{L1}$ of pure water, the surface tension $\gamma_{L2}$ of the aqueous solution used in the present embodiment, and the contact angles $\theta_1$ and $\theta_2$ can be measured. Here, since the tension $\gamma_S$ of the silicon wafer surface ($SiO_2$) is constant, the relationship between $\gamma_{SL1}$ and $\gamma_{SL2}$ can be determined. Here, the surface tension $\gamma_L$ of the liquid can be measured by the suspension method.

The aqueous solution used in the present embodiment is preferably at least one selected from the group consisting of a sodium chloride solution, a potassium chloride solution, and a magnesium chloride solution. This is because these aqueous solutions are easy to prepare and have an appropriate surface tension. The concentration of these aqueous solutions is not particularly limited, but from the viewpoint of achieving an appropriate surface tension, the concentration is preferably 10 mass % or more, with a concentration up to the solubility being tolerable as an upper limit.

The volume of the droplet during contact angle measurement is preferably set within a range of 0.3 μL to 3.0 μL. The reason is that if the droplet volume is 0.3 μL or more, the effect of evaporation and volatilization of the droplet is small, and the error in contact angle measurement does not become large, while if the droplet volume is 3.0 μL or less, the droplet is not easily crushed by its own weight, and again the error in contact angle measurement does not become large.

The humidity of the environment in which the contact angle is measured is preferably in a range of 30% RH to 70% RH. The reason is that if the humidity is 30% RH or higher, the effect of evaporation and volatilization of the droplet is small, and the error in contact angle measurement does not become large, while if the humidity is 70% RH or lower, the water molecules adsorbed on the silicon wafer surface due to condensation will not increase excessively, and again the error in contact angle measurement does not become large.

While the details are explained in the Examples with reference to FIG. 2, in the present embodiment, the contact angle of the surface of the silicon wafer is preferably measured under a plurality of conditions in which a volume of a droplet dripped on the surface differs to determine the relationship between volumes of the droplet and measured values of the contact angle under the plurality of conditions. We discovered that differences in the severe hydrophilicity level can also be detected as differences in the dependence of the contact angle on the droplet volume. In other words, we discovered that for wafers with a degraded severe hydrophilicity level, the ratio of change in contact angle to change in droplet volume is large, and for wafers with a superior severe hydrophilicity level, the ratio of change in contact angle to change in droplet volume is small. Therefore, as illustrated in FIG. 2, the measured data can be plotted on a plane with the droplet volume on the horizontal axis and the contact angle on the vertical axis to detect differences in hydrophilicity level based on the dependence of the contact angle on the droplet volume.

At this time, the volume (amount) of the actually dripped droplet is preferably measured (calculated) from an image of the droplet. Although the droplet volume can be set on the contact angle meter that is used, some degree of error may occur between the device setting of the droplet volume and the actual volume of the droplet that is dripped. Therefore, the dependence of the contact angle on the droplet volume can more accurately be determined by plotting the actual measured droplet volume, rather than the device setting.

From the viewpoint of more accurately determining the dependence of the contact angle on the droplet volume, the contact angle is preferably measured under 3 or more conditions in which the volume of the droplet differs, and more preferably under 5 or more conditions. Although no particular upper limit is placed on the number of conditions, the number of conditions can be 8 or less given that the accuracy reaches saturation.

(Method of Evaluating Surface Condition of Silicon Wafer)

A method of evaluating a surface condition of a silicon wafer according to an embodiment of the present disclosure includes the aforementioned method of measuring a contact angle of a silicon wafer according to an embodiment, and evaluating a surface condition of the silicon wafer based on a value of the measured contact angle.

For example, based on differences in the measured values of the contact angle, differences in the severe hydrophilicity level of the wafer surface can be detected, such differences not being detectable by contact angle measurement using pure water.

As described above, based on the dependence of the contact angle on the droplet volume, differences in the severe hydrophilicity level of the wafer surface can be detected, such differences not being detectable by contact angle measurement using pure water.

EXAMPLES

After mirror polishing, wafers were subjected to a pre-cleaning step of cleaning the wafers using a combination of an SC1 cleaning tank, an HF tank, an ozone tank, and the like and then rinsing the wafers with pure water and subsequently drying the wafers. Two single crystal silicon wafers (300 mm diameter) were thus prepared. It is thought that since drying after the pre-cleaning step was insufficient, water vapor was generated in the FOUP and adsorbed on the wafer surface, resulting in polarization of water molecules on the wafer surface for the 2 silicon wafers. A natural oxide film was formed on the surface layer of each of the 2 silicon wafers.

[Level 1]

One of the 2 silicon wafers was subjected to contact angle measurements by the following Example and Comparative Example immediately after removal from the FOUP.

[Level 2]

The other of the 2 silicon wafers was subjected to pretreatment by exposing the surface of the silicon wafer to downflow in a clean room and was then subjected to contact angle measurements according to the following Example and Comparative Example. In the pretreatment, the fan speed was 1300 rpm, and the process time was 300 seconds.

Both the Level 1 and Level 2 silicon wafers had a natural oxide film on the surface layer, and the wafer surface was basically hydrophilic. However, the Level 1 silicon wafer had a slightly lower level of hydrophilicity due to the polarization of water molecules, whereas the Level 2 silicon wafer was thought to have achieved a higher level of hydrophilicity due to the elimination of water molecule polarization by the pretreatment.

Example

The contact angle of the surface of each silicon wafer was measured by the θ/2 method under the following conditions. The 3 conditions below were used as the set droplet volume, and the actual droplet volume that was dripped was measured from images of the droplets.

Apparatus: PCA-11 portable contact angle meter manufactured by Kyowa Interface Science Co., Ltd.
Type of dripped liquid: 20 mass % NaCl aqueous solution
Set droplet volume: 3 conditions of 0.5 μL, 1.0 μL, 2.0 μL
Measurement points: 5 points on wafer surface (1 cm to 2 cm intervals from the center to the edge)
Ambient humidity: 40% RH Comparative Example The contact angle of the surface of each silicon wafer was measured by the θ/2 method under the following conditions. The 2 conditions below were used as the set droplet volume, and the actual droplet volume that was dripped was measured from images of the droplets.

Apparatus: PCA-11 portable contact angle meter manufactured by Kyowa Interface Science Co., Ltd.
Type of dripped liquid: pure water
Set droplet volume: 2 conditions of 1.0 μL, 2.0 μL
Measurement points: 5 points on wafer surface (1 cm to 2 cm intervals from the center to the edge)
Ambient humidity: 40% RH

[Measurement Results]

In the Example and the Comparative Example, the average value of the measured contact angle (average value of 5 points) and the average value of the measured droplet volume (average value of 5 points) were calculated for each set droplet volume. A graph plotting the measured data with the measured value of the droplet volume (average of 5 points) on the horizontal axis and the measured value of the contact angle (average of 5 points) on the vertical axis is illustrated in FIG. 2.

In the contact angle measurement based on the Comparative Example, the average contact angle was 5° or less for both Level 1 and Level 2, independent of the droplet volume. Contact angles of 5° or less are unreliable and are therefore represented as 5° in FIG. 2. By contrast, in the contact angle measurement based on the Example, the average contact angle was 21.9° for Level 1 and 19.8° for Level 2 in the case of a set droplet volume of 0.5 μL. In this way, the Example enabled detection of differences in the severe hydrophilicity level of the wafer surface, such differences not being detectable by contact angle measurement based on the Comparative Example.

Furthermore, it is clear from FIG. 2 that in the Example, the ratio of the change in contact angle to the change in droplet volume was large for Level 1, which had an inferior hydrophilicity level, whereas the ratio of the change in contact angle to the change in droplet volume was small for Level 2, which had a high hydrophilicity level. This indicates that the Example also enabled detection of differences in hydrophilicity level based on the dependence of the contact angle on the droplet volume.

Additional Experiment

Subsequently, for each of the Level 1 and Level 2 silicon wafers, single-wafer spin cleaning was performed by first performing spin cleaning with ozone water, followed by 3 sets of a combination of spin cleaning with hydrofluoric acid and subsequent spin cleaning with ozone water. Finally, spin drying was performed at a wafer rotation speed of 1500 rpm.

Conditions for spin cleaning with ozone water
- Concentration: 25 mg/L
- Flow rate: 1.0 L/min
- Process time per cleaning: 200 seconds
- Wafer rotation speed: 500 rpm Conditions for single-wafer spin cleaning with hydrofluoric acid
- Concentration: 1 mass %
- Flow rate: 1.0 L/min
- Process time per cleaning: 50 seconds
- Wafer rotation speed: 500 rpm The surface of each silicon wafer was then measured using a laser particle counter (manufactured by KLA-Tencor, Surfscan SP7) in high sensitivity (HS) mode to determine the number of LPDs 15 nm or greater in size. The Level 1 silicon wafer had an LPD count of 200, whereas the Level 2 silicon wafer had an LPD count of 5.

This indicates that the difference in the severe hydrophilicity level of the silicon wafer surface, which cannot be detected by contact angle measurement using pure water, produces the difference in the LPD count after single-wafer spin cleaning. The reason for this is thought to be as follows. Even if the difference in hydrophilicity level is so slight that it cannot be detected by contact angle measurement using pure water, in the initial step of single-wafer spin cleaning (for example, spin cleaning with ozone water) of a wafer with a degraded level of hydrophilicity, the cleaning solution does not spread evenly over the wafer surface, and the film of cleaning solution is not continuously maintained on the wafer surface; this results in local areas of the wafer surface that the cleaning solution does not reach, and as a result, particles remain after single-wafer spin cleaning, or etching irregularities occur after single-wafer spin cleaning, resulting in a higher LPD count.

In this regard, the Example enables detection, before single-wafer spin cleaning, of the difference in the severe hydrophilicity level of the silicon wafer surface that leads to the difference in the LPD count after single-wafer spin cleaning. Therefore, for silicon wafers that are determined to be inferior in severe hydrophilicity level as a result of contact angle measurement based on the Example, measures such as performing single-wafer spin cleaning after pretreatment to increase the hydrophilicity can be taken. In other words, the present disclosure can be considered an effective method for reliably reducing the LPD count after single-wafer spin cleaning.

INDUSTRIAL APPLICABILITY

The method of measuring the contact angle of a silicon wafer in the present disclosure enables detection of differences in the severe hydrophilicity level of the silicon wafer surface, such differences not being detectable by contact angle measurement using pure water.

The invention claimed is:

1. A method of measuring a contact angle of a silicon wafer, the method comprising:
dripping a droplet on a surface of a silicon wafer; and
measuring a contact angle of the surface of the silicon wafer from an image of the droplet,
wherein the droplet is composed of an aqueous solution having a surface tension greater than a surface tension of pure water.

2. The method of measuring a contact angle of a silicon wafer according to claim 1, wherein the aqueous solution is at least one selected from the group consisting of a sodium chloride solution, a potassium chloride solution, and a magnesium chloride solution.

3. The method of measuring a contact angle of a silicon wafer according to claim 1, wherein the aqueous solution has a concentration of 10 mass % or more.

4. The method of measuring a contact angle of a silicon wafer according to claim 1, wherein a volume of the droplet is in a range of 0.3 μL to 3.0 μL.

5. The method of measuring a contact angle of a silicon wafer according to claim 1, wherein the contact angle is measured in an environment with a humidity in a range of 30% RH to 70% RH.

6. The method of measuring a contact angle of a silicon wafer according to claim 1, further comprising measuring the contact angle of the surface of the silicon wafer under a plurality of conditions in which a volume of a droplet dripped on the surface differs and determining a relationship between the volumes of the droplet and measured values of the contact angle under the plurality of conditions.

7. The method of measuring a contact angle of a silicon wafer according to claim 6, wherein the volume of the droplet is measured from the image of the droplet.

8. The method of measuring a contact angle of a silicon wafer according to claim 1, wherein the silicon wafer includes a surface layer that is an oxide film, and the oxide film forms the surface.

9. The method of measuring a contact angle of a silicon wafer according to claim 8, wherein the oxide film is a natural oxide film.

10. A method of evaluating a surface condition of a silicon wafer, the method comprising:

the method of measuring a contact angle of a silicon wafer according to claim 1; and evaluating a surface condition of the silicon wafer based on a value of the measured contact angle.

* * * * *